United States Patent
Adachi (10) Patent No.: US 7,659,518 B2
(45) Date of Patent: Feb. 9, 2010

(54) LIGHT OR RADIATION IMAGE PICKUP APPARATUS

(75) Inventor: Susumu Adachi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 12/375,189

(22) PCT Filed: Jul. 27, 2006

(86) PCT No.: PCT/JP2006/314892

§ 371 (c)(1),
(2), (4) Date: Jan. 26, 2009

(87) PCT Pub. No.: WO2008/012897

PCT Pub. Date: Jan. 31, 2008

(65) Prior Publication Data

US 2009/0184253 A1 Jul. 23, 2009

(51) Int. Cl.
H01L 27/146 (2006.01)
(52) U.S. Cl. .................................. 250/370.09; 378/98.8
(58) Field of Classification Search ............ 250/370.09; 378/98.8
See application file for complete search history.

(56) References Cited

U.S. PATENT DOCUMENTS

| 6,343,112 B1 | 1/2002 | Petrick et al. |
| 2004/0017891 A1 | 1/2004 | Endo |

FOREIGN PATENT DOCUMENTS

| JP | 2000-324401 A | 11/2000 |
| JP | 2002-202377 A | 7/2002 |
| JP | 2002-243860 A | 8/2002 |
| JP | 2003-265453 A | 9/2003 |
| JP | 2003-319264 A | 11/2003 |
| JP | 2004-023750 A | 1/2004 |
| JP | 2004-080410 A | 3/2004 |
| JP | 2004-080749 A | 3/2004 |
| JP | 2005064307 A * | 3/2005 |
| JP | 2005-269441 A | 9/2005 |
| JP | 2006-516179 A | 6/2006 |
| WO | WO-2004/036738 A2 | 4/2004 |

OTHER PUBLICATIONS

International Search Report for the Application No. PCT/JP2006/314892 mailed Oct. 31, 2006.

* cited by examiner

Primary Examiner—David P Porta
Assistant Examiner—Marcus H Taningco
(74) Attorney, Agent, or Firm—Cheng Law Group, PLLC (57) ABSTRACT

A light or radiation image pickup apparatus comprises a first arithmetic unit 50 for calculating a first arithmetic value by subtracting a first offset signal from a main signal, a second arithmetic unit 51 for calculating a second arithmetic value which is a difference between a second offset signal and the first offset signal, and a correcting unit 52 for correcting the first arithmetic value calculated by the first arithmetic unit 50, by using the second arithmetic value calculated by the second arithmetic unit 51 and corresponding to a period of the same length as a period from the first offset signal to the main signal used in the operation in the first arithmetic unit 50. The first arithmetic value is corrected to remove noise components due to leakage of charge signals accumulated during the period from the first offset signal to the main signal. It is thus possible to reduce deterioration of image quality due to leaks of charge signals accumulated in X-ray detecting elements 11 (leakage currents) and prevent an extended imaging time.

9 Claims, 6 Drawing Sheets

LIGHT OR RADIATION IMAGE PICKUP APPARATUS

TECHNICAL FIELD

This invention relates to a light or radiation image pickup apparatus for use in the medical field or industrial field such as in non-destructive testing, RI (Radio Isotope) inspection and optical inspection, and more particularly to a technique for reading charge signals from detecting elements that detect light or radiation.

BACKGROUND ART

Conventionally, an image pickup apparatus that picks up images based on light or radiation detected has a light or radiation detector for detecting light or radiation. An X-ray detector will be described by way of example here. An X-ray detector has an X-ray sensitive X-ray conversion layer (X-ray conversion film). The X-ray conversion layer converts incident X rays into carriers (charge signals), and the X rays are detected by reading the converted charge signals. For example, the X-ray detector includes a plurality of X-ray detecting elements arranged vertically and horizontally in a two-dimensional matrix form, charge detecting and amplifying circuits (CSA: Charge Sensitive Amplifiers) for converting charge signals converted by the X-ray detecting elements into voltage signals, signal amplifying circuits for amplifying the voltage signals from the charge detecting and amplifying circuits, and a sample hold circuit for sampling the voltage signals outputted from the signal amplifying circuits, holding the sampled voltage signals and outputting them to an A/D converter.

Further, the X-ray detecting elements include collecting electrodes for collecting the charge signals converted by the X-ray conversion layer based on a bias voltage applied from a common electrode, capacitors for storing the charge signals collected by the collecting electrodes, thin-film transistors (TFT: Thin Film Transistors) acting as switching elements, gate lines for controlling the thin-film transistors from a gate driver, and data lines for reading the charge signals from the thin-film transistors.

When X rays are emitted to a patient M to carry out X-ray imaging, an X-ray image transmitted through the patient M is projected to an amorphous selenium film to generate charge signals proportional to the density of the image in the film. Subsequently, the charge signals generated in the film are collected by the carrier collecting electrodes, and the charge signals collected by the collecting electrodes are stored in the capacitors. Further, the charge signals stored in the capacitors are outputted to the charge detecting and amplifying circuits by switching operation of the thin-film transistors (TFTs).

Although, in such construction, the charge signals accumulated in the capacitors of the X-ray detector are outputted to the charge detecting and amplifying circuits by switching operation of the thin-film transistors, even when the thin-film transistors are in OFF state, the OFF state is imperfect and slight leaks of the charge signals (leakage currents) occur from the capacitors. Where numerous detecting elements are connected to the data lines through which the charge signals are read from the thin-film transistors, the leaks of the charge signals will increase with the number of these detecting elements, thereby increasing the influence imparted to image quality. That is, artifacts will occur due to the leaks of the charge signals, causing a problem of lowering image quality. In order to solve this problem, the thin-film transistors of all the detecting elements connected to each gate line are first switched to ON state successively by control from the gate driver, to collect data (charge signals) from all the detecting elements including the leakage currents. Then, the data (charge signals) from all the detecting elements corresponding to the leakage currents is collected, and the charge signals only for the leakage currents are subtracted from the charge signals from all the detecting elements including the leakage currents, thereby reducing the influence of the leaks of the charge signals from the capacitors (see Patent Documents 1 and 2, for example).

[Patent Document 1]
Unexamined Patent Publication No. 2004-23750
[Patent Document 2]
Unexamined Patent Publication No. 2003-319264

DISCLOSURE OF THE INVENTION

Problem to be Solved by the Invention

However, the conventional light or radiation image pickup apparatus has the following problem. That is, the thin-film transistors of all the detecting elements connected to each gate line are switched to ON state successively by control from the gate driver, to collect data (charge signals) from all the detecting elements including the leakage currents. Then, the data (charge signals) from all the detecting elements corresponding to the leakage currents is collected, and the charge signals only for the leakage currents are subtracted from the charge signals from all the detecting elements including the leakage currents. In such a case, an extra time is need for collecting the data (charge signals) from all the detecting elements which corresponds to the leakage currents, posing a problem of an extended imaging time.

This invention has been made having regard to the state of the art noted above, and its object is to provide a light or radiation image pickup apparatus which can reduce deterioration of image quality due to leaks of charge signals stored in the detecting elements of an X-ray detector (leakage currents), and prevent an extended imaging time.

Means for Solving the Problem

To fulfill this object, this invention provides the following construction.

A light or radiation image pickup apparatus of this invention comprises (A) a plurality of detecting devices arranged in a matrix form for outputting charge signals in response to light or radiation, (B) a plurality of charge-to-voltage conversion devices the respective charge signals outputted from the plurality of detecting devices into voltage signals, (C) an A/D conversion device for receiving, sampling with predetermined timing and converting into digital voltage signals, the voltage signals converted by the plurality of charge-to-voltage conversion devices, (D) a control device for controlling the detecting devices to output the charge signals, (E) a plurality of gate lines commonly connecting the control device and the detecting devices arranged in rows, among the plurality of detecting device arranged in the matrix form, (F) a first arithmetic device for calculating a first arithmetic value by subtracting, from a main signal which is a digital voltage signal converted by the A/D conversion device immediately after the control device finishes control of the detecting devices connected to one predetermined gate line among the plurality of gate lines, a first offset signal which is a digital voltage signal converted by the A/D conversion device immediately before the control device starts the control of the detecting devices, (G) a second arithmetic device for calculating a second arithmetic value which is a difference between a second offset signal which is a digital voltage signal converted by the A/D conversion device immediately before the control device starts control of the detecting devices connected to one predetermined gate line, adjacent the gate line used in the operation in the first arithmetic device, among the plurality of gate lines, and the first offset signal used in the operation in the first arithmetic device, and (H) a correcting device for correcting the first arithmetic value calculated by the first arithmetic device, by using the second arithmetic value calculated by the second arithmetic device and corresponding to a period of the same length as a period from the first offset signal to the main signal used in the operation in the first arithmetic device.

The functions of the invention in claim 1 are as follows. First, when light or radiation impinges on the plurality of detecting devices arranged in a matrix form, these detecting devices outputs charge signals in response to this incident light or radiation. Further, the charge signals outputted from the detecting devices are converted into voltage signals by the charge-to-voltage conversion devices. The A/D conversion device receives the voltage signals converted by the charge-to-voltage conversion device, samples them with predetermined timing and converts them into digital voltage signals.

The control device controls the detecting devices to output the charge signals. Here, the control device and the detecting devices arranged in rows, among the plurality of detecting devices arranged in the matrix form are commonly connected by a plurality of gate lines. The first arithmetic device calculates a first arithmetic value by subtracting, from a main signal which is a digital voltage signal converted by the A/D conversion device immediately after the control device finishes control of the detecting devices connected to one predetermined gate line among the plurality of gate lines, a first offset signal which is a digital voltage signal converted by the A/D conversion device immediately before the control device starts the control of the detecting devices. That is, the first arithmetic value becomes a value without noise component signal (first offset signal) included in the main signal. Further, the second arithmetic device calculates a second arithmetic value which is a difference between a second offset signal which is a digital voltage signal converted by the A/D conversion device immediately before the control device starts control of the detecting devices connected to one predetermined gate line, adjacent the gate line used in the operation in the first arithmetic device, among the plurality of gate lines, and the first offset signal used in the operation in the first arithmetic device. That is, the second arithmetic value is a value of leaks of the charge signals (leakage currents) accumulated during the period between the second offset signal and the first offset signal. The correcting device corrects the first arithmetic value calculated by the first arithmetic device, by using the second arithmetic value calculated by the second arithmetic device and corresponding to a period of the same length as a period from the first offset signal to the main signal used in the operation in the first arithmetic device. That is, the first arithmetic value is corrected to remove noise components due to leakage of charge signals accumulated during the period from the first offset signal to the main signal.

It is thus possible to reduce deterioration of image quality due to leaks of charge signals accumulated in the detecting devices (leakage currents) and prevent an extended imaging time.

The light or radiation image pickup apparatus of the invention in claim 2, in the light or radiation image pickup apparatus according to claim 1, further comprises, as arranged between the charge-to-voltage conversion device and the A/D conversion device, a lowpass filter for restricting passage of signals of high frequency band components, and a holding device for sampling, and holding for a predetermined time, the voltage signals having passed the lowpass filter.

According to the light or radiation image pickup apparatus of the invention in claim 2, the lowpass filter restricts passage of signals of high frequency band components (high frequency noise) in the voltage signals converted by the charge-to-voltage conversion devices, and the holding device samples the voltage signals having passed this low-pass filter, and holds them for a predetermined time. Further, stable analog voltage signals from this holding device are converted into digital voltage signals. That is, the A/D conversion device converts the stable analog voltage signals into digital voltage signals. It is also possible to reduce high frequency noise inputted to the A/D conversion device, increase the S/N ratio, and obtain high-precision images.

The light or radiation image pickup apparatus of the invention in claim 3, in the light or radiation image pickup apparatus according to claim 1, further comprises a multiplexer for receiving each of the voltage signals converted by the plurality of charge-to-voltage conversion devices, temporally switching the received voltage signals in a predetermined order, and outputting a time sharing signal bundling the voltage signals converted by each of the different charge-to-voltage conversion devices, wherein the A/D conversion device samples, with predetermined timing, and converts into each voltage signal of a digital time sharing signal, each voltage signal of the time sharing signal outputted from the multiplexer.

According to the light or radiation image pickup apparatus of the invention in claim 3, the multiplexer receives each of the voltage signals converted by the plurality of charge-to-voltage conversion devices, temporally switches the received voltage signals in a predetermined order, and outputs a time sharing signal bundling the voltage signals converted by each of the different charge-to-voltage conversion devices. Further, the A/D conversion device samples, with predetermined timing, each voltage signal of the time sharing signal outputted from the multiplexer, and converts it into each voltage signal of a digital time sharing signal. Therefore, with only one A/D conversion device provided for the plurality of charge-to-voltage conversion devices, conversion can be made from the analog voltage signals to the digital voltage signals, which realizes a reduction in the cost of conversion to the digital voltage signals.

The light or radiation image pickup apparatus of the invention in claim 4, in the light or radiation image pickup apparatus according to claim 1, has A/D conversion devices corresponding in number to the plurality of charge-to-voltage conversion devices.

According to the light or radiation image pickup apparatus of the invention in claim 4, the A/D conversion devices correspond in number to the plurality of charge-to-voltage conversion devices. Thus, compared with the case of providing only one A/D conversion device for the plurality of charge-to-voltage conversion devices, the processing time in the A/D conversion devices can be shortened.

The light or radiation image pickup apparatus of the invention in claim 5, in the light or radiation image pickup apparatus according to claim 1, has at least one of the main signal, the first offset signal and the second offset signal sampled a plurality of times to obtain an average value thereof.

According to the light or radiation image pickup apparatus of the invention in claim 5, at least one of the main signal, the first offset signal and the second offset signal is sampled a plurality of times to obtain an average value thereof. Thus, variations in at least one signal among the main signal, first offset signal and second offset signal can be reduced to enable correction based on a high-precision value. As a result, the value corrected by the correcting device can be highly accurate.

The light or radiation image pickup apparatus of the invention in claim 6, in the light or radiation image pickup apparatus according to claim 1, has filtering applied to at least one of the first arithmetic value in the first arithmetic device, the second arithmetic value in the second arithmetic device, and the first arithmetic value corrected by the correcting device.

According to the light or radiation image pickup apparatus of the invention in claim 6, by filtering at least one of the first arithmetic value in the first arithmetic device, the second arithmetic value in the second arithmetic device, and the first arithmetic value corrected by the correcting device, it is possible to obtain optimal first arithmetic value, second arithmetic value, and the first arithmetic value corrected by the correcting device.

The light or radiation image pickup apparatus of the invention in claim 7, in the light or radiation image pickup apparatus according to claim 1, has the second arithmetic value in the second arithmetic device put to an averaging process using second arithmetic values in the second arithmetic device acquired in the past.

According to the light or radiation image pickup apparatus of the invention in claim 7, the second arithmetic value in the second arithmetic device put to an averaging process using second arithmetic values in the second arithmetic device acquired in the past. Thus, an optimal second arithmetic value can be obtained, and an optimal first arithmetic value corrected by the correcting device can be obtained based on this averaged, second arithmetic value.

The light or radiation image pickup apparatus of the invention in claim 8, in the light or radiation image pickup apparatus according to claim 1, has the period from the second offset signal to the first offset signal used in the operation in the second arithmetic device being the power of two of the period from the first offset signal to the main signal used in the operation in the first arithmetic device.

According to the light or radiation image pickup apparatus of the invention in claim 8, the period from the second offset signal to the first offset signal used in the operation in the second arithmetic device is the power of two of the period from the first offset signal to the main signal used in the operation in the first arithmetic device. This simplifies a division process, thereby increasing the processing speed.

In the light or radiation image pickup apparatus of the invention in claim 9, the detecting devices have switching elements for outputting the charge signals based on the control of the control device, the switching elements being thin-film transistors.

According to the light or radiation image pickup apparatus of the invention in claim 9, the switching elements are thin-film transistors. Therefore, compared with switching elements such as MOSFETs, there is little deterioration of the switching elements per se due to irradiation of light or radiation. That is, use can be made for a long time. By providing a plurality of detecting devices, a detection area can be enlarged.

Effects of the Invention

According to the light or radiation image pickup apparatus of this invention, the correcting device corrects the first arithmetic value calculated by the first arithmetic device, by using the second arithmetic value calculated by the second arithmetic device and corresponding to a period of the same length as a period from the first offset signal to the main signal used in the operation in the first arithmetic device. That is, the first arithmetic value is corrected to remove noise components due to leakage of charge signals accumulated during the period from the first offset signal to the main signal. It is thus possible to reduce deterioration of image quality due to leaks of charge signals accumulated in the detecting devices (leakage currents) and prevent an extended imaging time.

DESCRIPTION OF REFERENCES

4 . . . A/D converter (A/D conversion device)
11 . . . X-ray detecting elements (detecting devices)
12 . . . X-ray detection controller (control device)
21 . . . thin-film transistors
31 . . . charge detecting and amplifying circuits (charge-to-voltage conversion devices)
33 . . . sample hold circuit (holding device)
34 . . . lowpass filter
36 . . . multiplexer
50 . . . first arithmetic unit (first arithmetic device)
51 . . . second arithmetic unit (second arithmetic device)
52 . . . correcting unit (correcting device)
GL1-GL5 . . . gate lines

BEST MODE FOR CARRYING OUT THE INVENTION

The object to reduce deterioration of image quality due to leaks of charge signals accumulated in detecting devices (leakage currents) and prevent an extended imaging time has been fulfilled.

EMBODIMENT

Figure 1:
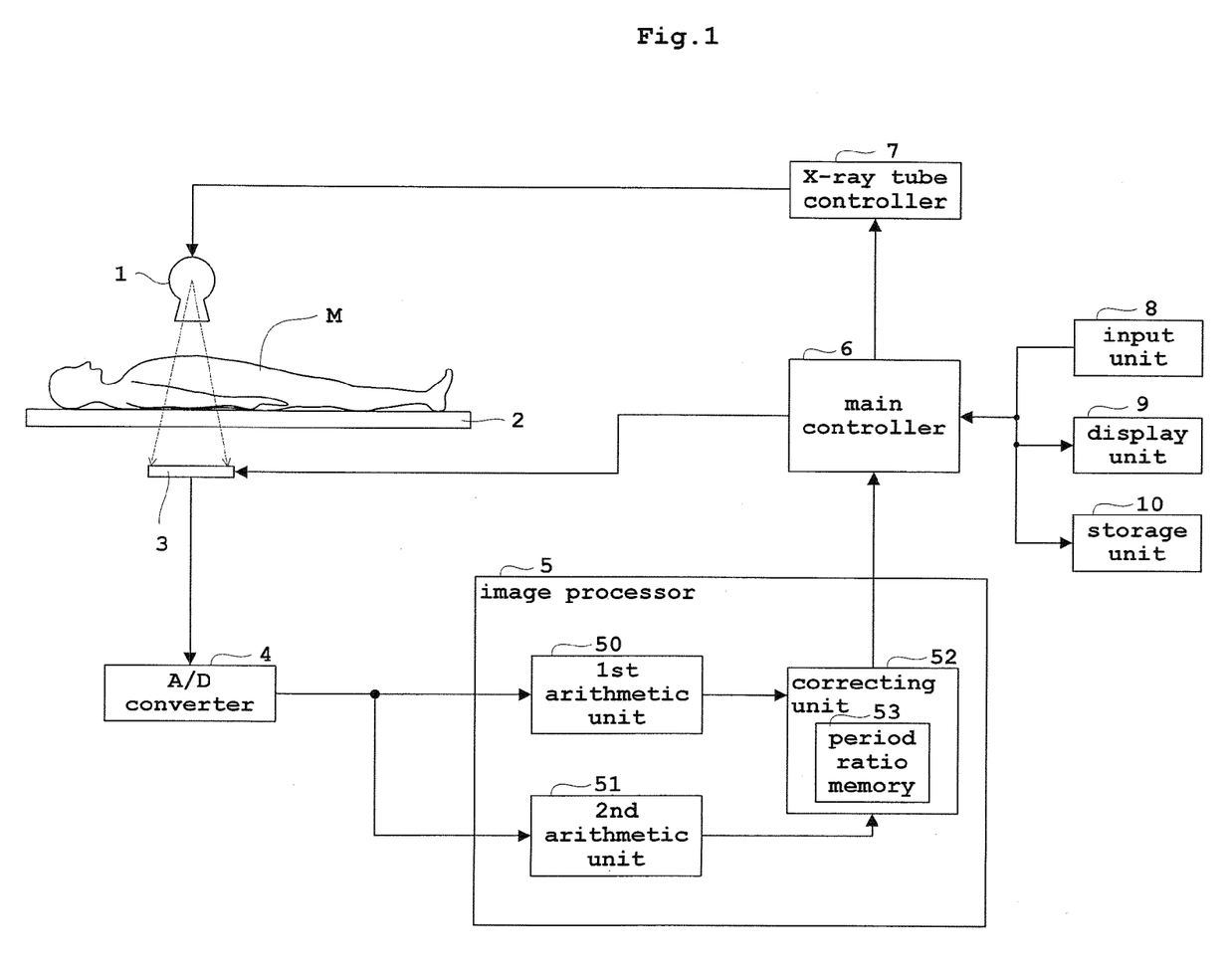
FIG. 1 is a block diagram showing an overall construction of an X-ray image pickup apparatus.
Figure 2:
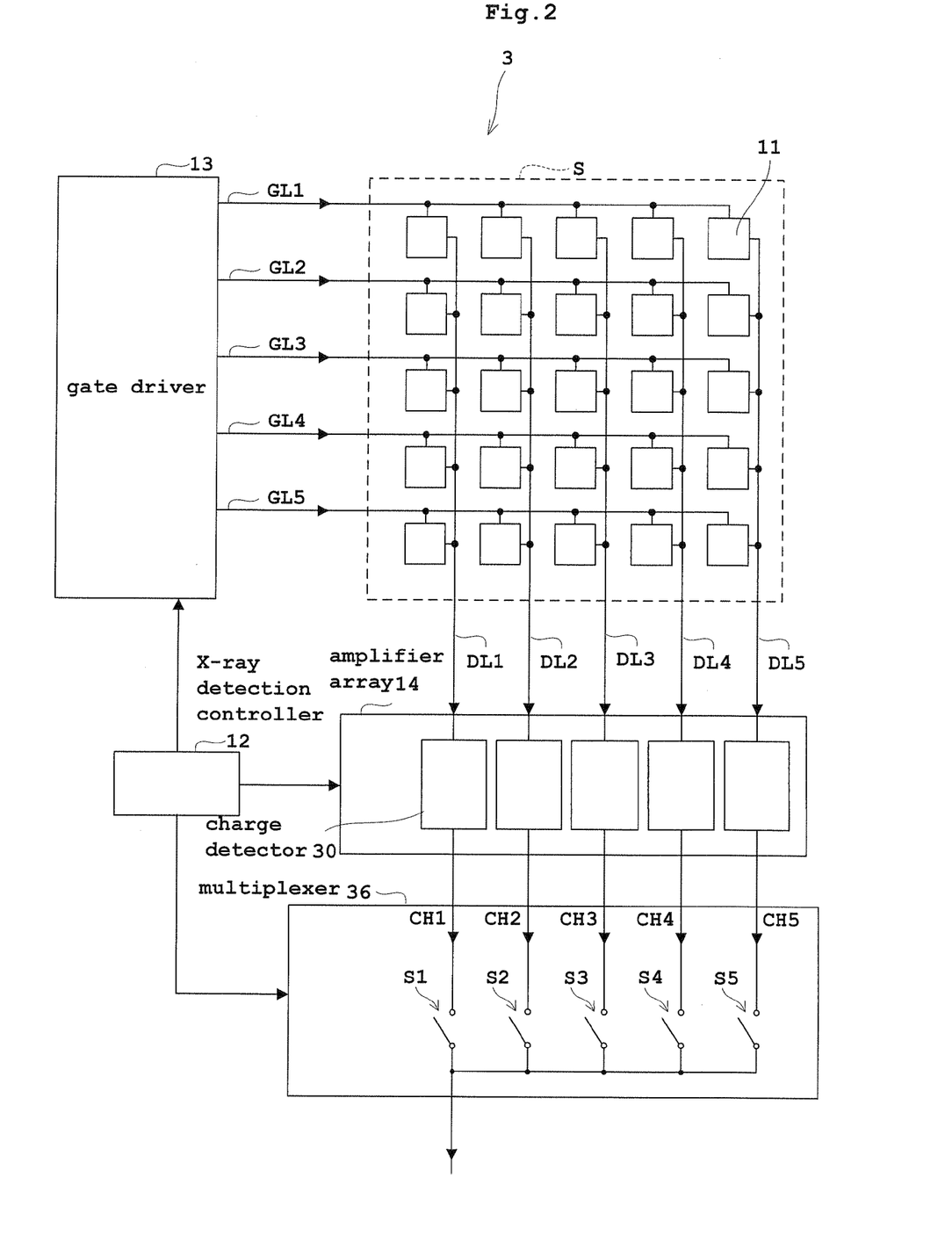
FIG. 2 is a block diagram showing an X-ray detector.
Figure 3:
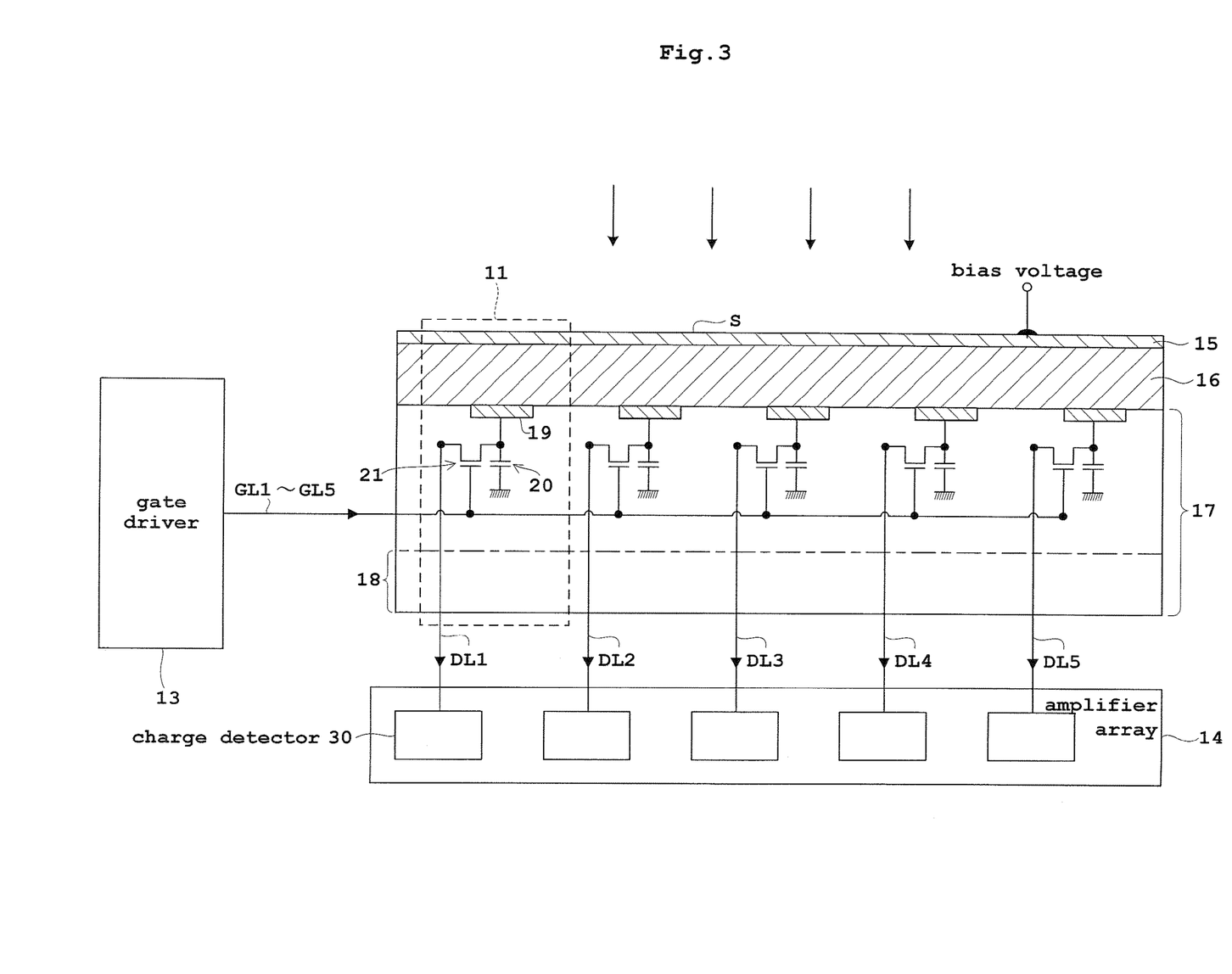
FIG. 3 is a sectional view showing a construction of X-ray detecting elements.
Figure 4:
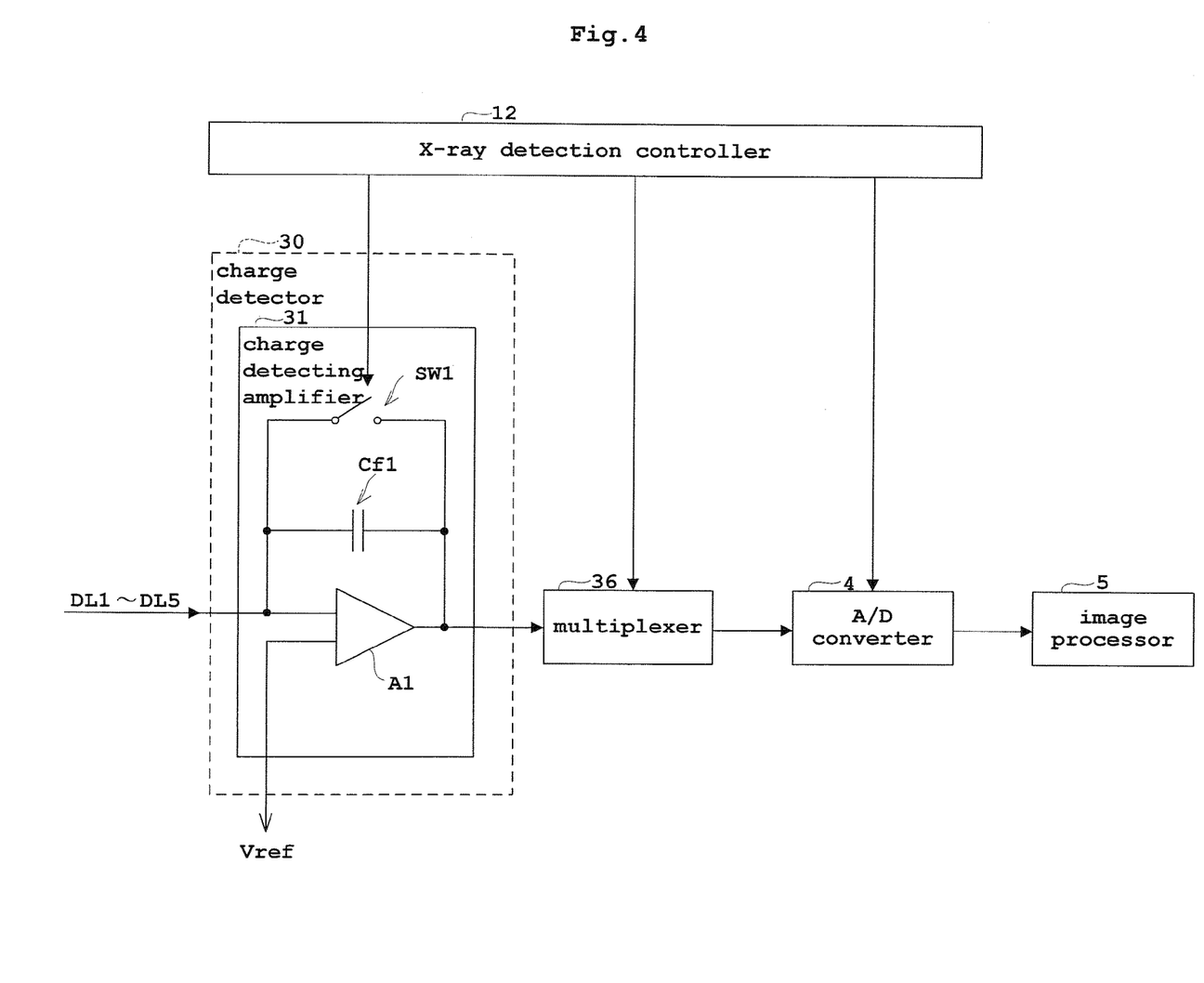
FIG. 4 is a block diagram showing a charge detector.

An X-ray image pickup apparatus will be described as an example of light or radiation image pickup apparatus in the embodiment. This X-ray image pickup apparatus will be described hereinafter with reference to the drawings. FIG. 1 is a block diagram showing an overall construction of the X-ray image pickup apparatus. FIG. 2 is a block diagram showing an X-ray detector. FIG. 3 is a sectional view showing a construction of X-ray detecting elements. FIG. 4 is a block diagram showing a charge detector.

As shown in FIG. 1, the X-ray image pickup apparatus includes an X-ray tube 1 for emitting X rays to a patient M to be imaged, a top board 2 for supporting the patient M, an X-ray detector 3 for converting to charge signals corresponding to the quantity of X rays transmitted through the patient M (i.e. detecting X rays as charge signals) and further converting the charge signals into voltage signals for output, an A/D converter 4 for converting the voltage signals outputted from the X-ray detector 3 into digital voltage signals, an image processor 5 for processing and imaging the digital voltage signals converted by the A/D converter 4, a main controller 6 for carrying out various controls relating to X-ray imaging, an X-ray tube controller 7 for controlling the X-ray tube 1 by generating a tube voltage and a tube current based on the controls by the main controller 6, an input unit 8 capable of inputting settings relating to X-ray imaging, a display unit 9 for displaying X-ray images processed and produced by the image processor 5 and other information, and a storage unit 10 for storing the X-ray images processed and produced by the image processor 5 and other information. Each component of the X-ray image pickup apparatus will be further described in detail. The above A/D converter 4 corresponds to the A/D conversion device in this invention.

The X-ray tube 1 is disposed opposite the X-ray detector 3 across the patient M placed on the top board 2. As shown in FIG. 2, the X-ray detector 3 has a plurality of X-ray detecting elements 11, an X-ray detection controller 12, a gate driver 13, an amplifier array 14 and a multiplexer 36. The plurality of X-ray detecting elements 11 are connected to the gate driver 13 by gate lines GL1-GL5, and are connected to the amplifier array 14 by data lines DL1-DL5. Further, the amplifier array 14 is connected to the multiplexer 36. The X-ray detection controller 12 is connected to the gate driver 13 and amplifier array 14.

The X-ray detecting elements 11 output charge signals in response to incident X rays, and are arranged vertically and horizontally in a two-dimensional matrix form (in rows and columns) on an X-ray detection surface S on which X rays impinge. For example, the X-ray detecting elements 11 are arranged in a two-dimensional matrix form in the order of 4096 rows (horizontal)×4096 columns (vertical) on the actual X-ray detection surface S. FIG. 2 shows, as an example, X-ray detecting elements 11 arranged in the two-dimensional matrix form of five rows×five columns. The plurality of gate lines GL1-GL5 commonly connect the gate driver 13 (X-ray detection controller 12) and the X-ray detecting elements 11 arranged in rows among the plurality of X-ray detecting elements 11 arranged in the matrix form. As shown in FIG. 3, the X-ray detecting elements 11 have a common electrode 15 for applying a bias voltage of high voltage, an X-ray conversion layer 16 for converting incident X rays into charge signals, and an active matrix substrate 17 for collecting, accumulating, and reading (outputting) the charge signals converted by the X-ray conversion layer 16.

The X-ray conversion layer 16 consists of an X-ray sensitive semiconductor, and amorphous selenium (a-Se), for example, is laminated planarly on the surface of this X-ray conversion layer 16. It is constructed such that, when X rays impinge on the X-ray conversion layer 16, a predetermined number of carriers (charge signals) proportional to the energy of X rays are generated directly (direct conversion type).

As shown in FIG. 3, the active matrix substrate 17 has a glass substrate 18, and on this glass substrate 18 are collecting electrodes 19 for collecting the charge signals converted by the X-ray conversion layer 16 based on the bias voltage applied from the common electrode 15, capacitors 20 for accumulating the charge signals collected by the collecting electrodes 19, thin-film transistors (TFT: Thin Film Transistors) 21 acting as switching elements, gate lines GL1-GL5 for controlling the thin-film transistors 21 from the gate driver 13, and data lines DL1-DL5 for reading the charge signals from the thin-film transistors 21. The above X-ray detecting elements 11 correspond to the detecting devices in this invention.

Next, the X-ray detection controller 12 is controlled from the main controller 6 (see FIG. 1), as shown in FIG. 2, carries out overall control of the gate driver 13, amplifier array 14, multiplexer 36 and A/D converter 4, and carries out controls to take out of the amplifier array 14 successively and selectively the charge signals detected by all the X-ray detecting elements 11, and to output them successively from the multiplexer 36. Specifically, the X-ray detection controller 12 is constructed to output a gate actuating signal for starting operation of the gate driver 13, an amplifier actuating signal for starting operation of the amplifier array 14, a multiplexer control signal for controlling operation of the multiplexer 36, and an A/D conversion control signal for controlling operation of the A/D converter 4. The above X-ray detection controller 12 corresponds to the control device in this invention for carrying out controls for starting operation of the gate driver 13, and for causing the X-ray detecting elements 11 to output the charge signals.

Next, the gate driver 13 operates the thin-film transistor 21 of each X-ray detecting element 11 to take out successively and selectively the charge signals detected by all the X-ray detecting elements 11. More particularly, the gate driver 13 operates successively and selectively the gate lines GL1-GL5 based on the gate actuating signal from the X-ray detection controller 12. The thin-film transistors 21 of X-ray detecting elements 11 connected to the gate line operated are turned on all at once, to output the charge signals accumulated in the capacitors 20 to the amplifier array 14 through the data lines DL1-DL5. The above charge detecting amplifier 31 corresponds to the charge-to-voltage conversion device in this invention.

Next, as shown in FIG. 2, the amplifier array 14 includes charge detectors 30 corresponding in number (five in FIG. 2) to the data lines DL1-DL5. As shown in FIG. 4, each charge detector 30 has a charge detecting amplifier (CSA: Charge Sensitive Amplifier) 31 for receiving the charge signals outputted from each X-ray detecting element 11 and converting them into voltage signals.

The charge detectors 30 in the amplifier array 14 shown in FIG. 2 is constructed to be operable based on the amplifier actuating signal from the X-ray detection controller 12. Specifically, based on the amplifier actuating signal from the X-ray detection controller 12, the charge detecting amplifier 31 of the charge detector 30 shown in FIG. 4 converts the charge signals into voltage signals, and outputs them to the multiplexer 36.

Further, the electrical structure of the charge detector 30 will be described in detail using FIG. 4. As shown in FIG. 4, the charge detecting amplifier 31 of the charge detector 30 is an amplifying element having an operational amplifier A1 with an inverting input terminal connected to data line DL1-DL5, a feedback capacitor $Cf_1$ disposed between the inverting input terminal and an output terminal of this operational amplifier A1, and a switch SW1 provided in parallel with this feedback capacitor $Cf_1$. A reference voltage Vref is applied to a non-inverting input terminal of the operational amplifier A1. The reference voltage Vref is at grounding level (0 [V]).

The switch SW1 changes to a conduction state and a cut-off state based on control from the X-ray detection controller 12. Specifically, the switch SW1 becomes the conduction state at a predetermined time based on the amplifier actuating signal from the X-ray detection controller 12. When the switch SW1 is in the conduction state, electric charges (charge signals) accumulated in the feedback capacitor $Cf_1$ are discharged, the feedback capacitor $Cf_1$ becomes a reset state, and the charge detecting amplifier 31 becomes an initialized state. After the predetermined time, at and after the switch SW1 is released from the cut-off state, i.e. the initialized state, the charge signals inputted from the data lines DL1-DL5 are accumulated. Thus, the charge detecting amplifier 31 has a construction for outputting voltages according to the charge signals inputted at and after a time of the initialized state being canceled.

Next, as shown in FIG. 2, the multiplexer 36 has switches S1-S5 corresponding in number (five in FIG. 2) to the number of charge detectors 30. Based on the multiplexer control signal from the X-ray detection controller 12, the switches S1-S5 are switched to ON state one after another, to output to the A/D converter 4 shown in FIG. 4 a time sharing signal which bundles each of the voltage signals (CH1-CH5) outputted from the charge detectors 30 (five here).

Next, the A/D converter 4 samples each voltage signal in the time sharing signal from the multiplexer 36, with predetermined timing based on the A/D conversion control signal from the X-ray detection controller 12, converts it into each voltage signal of a digital time sharing signal, and outputs it to the image processor 5.

As shown in FIG. 1, the image processor 5 includes a first arithmetic unit 50, a second arithmetic unit 51 and a correcting unit 52. The first arithmetic unit 50 calculates a first arithmetic value by subtracting, from a main signal which is a digital voltage signal converted by the A/D converter 4 immediately after the X-ray detection controller 12 finishes control of X-ray detecting elements 11 connected to one predetermined gate line among the plurality of gate lines, a first offset signal which is a digital voltage signal converted by the A/D converter 4 immediately before the X-ray detection controller 12 starts the control of these X-ray detecting elements 11.

The second arithmetic unit 51 calculates a second arithmetic value which is a difference between a second offset signal which is a digital voltage signal converted by the A/D converter 4 immediately before the X-ray detection controller 12 starts control of X-ray detecting elements 11 connected to one predetermined gate line, adjacent the gate line used in the operation in the first arithmetic unit 50, among the plurality of gate lines, and the first offset signal used in the operation in the first arithmetic unit 50.

The correcting unit 52 corrects the first arithmetic value calculated by the first arithmetic unit 50, by using the second arithmetic value calculated by the second arithmetic unit 51 and corresponding to a period of the same length as a period from the first offset signal to the main signal used in the operation in the first arithmetic unit 50. The correcting unit 52 has a period ratio memory 53 for storing a ratio of a period from the second offset signal to the first offset signal used in the operation in the second arithmetic unit 51, to the period from the first offset signal to the main signal used in the operation in the first arithmetic unit 50. The first arithmetic unit 50 noted above corresponds to the first arithmetic device in this invention. The second arithmetic unit 51 noted above corresponds to the second arithmetic device in this invention. The correcting unit 52 noted above corresponds to the correcting device in this invention.

Figure 5:
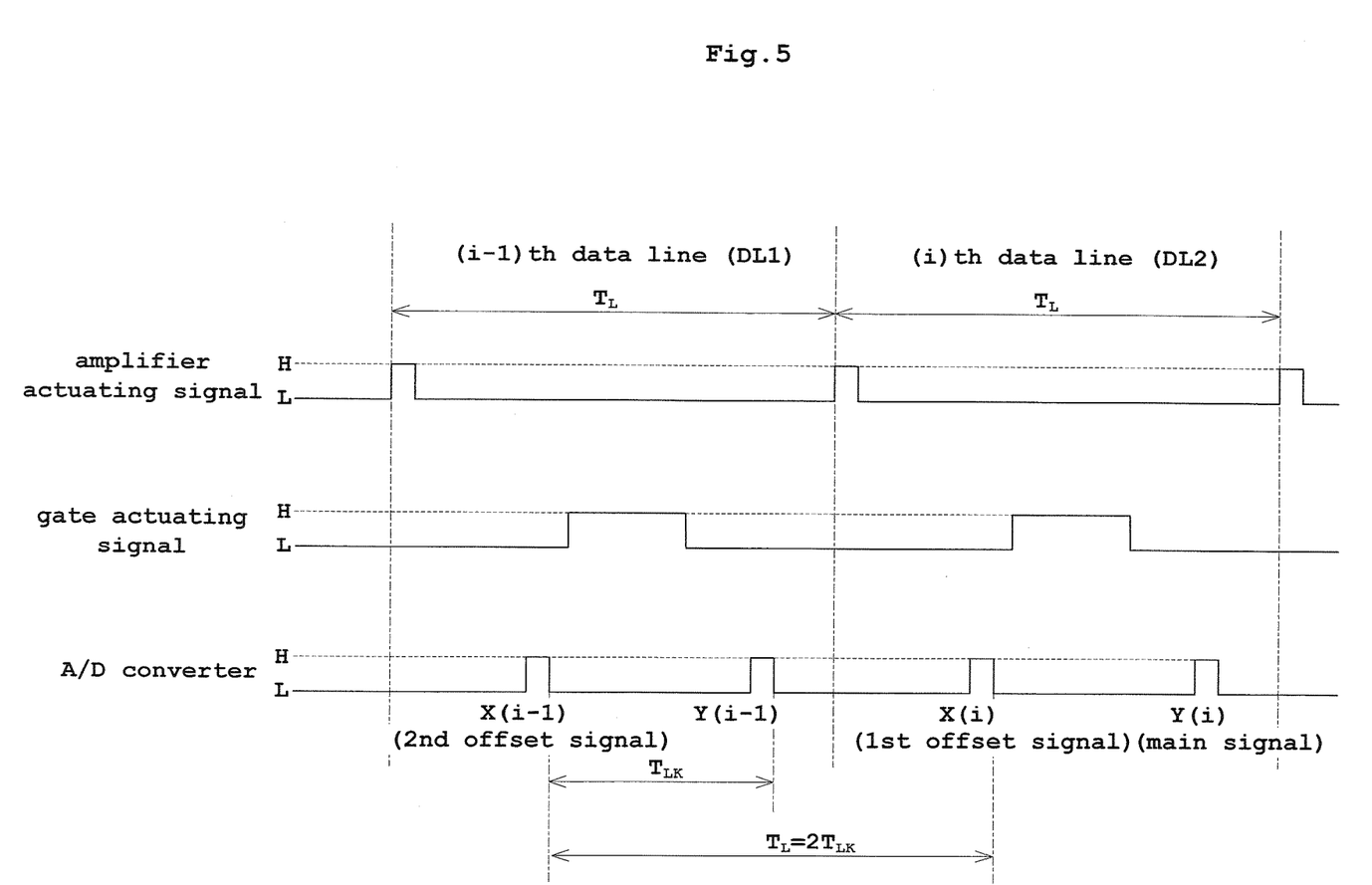
FIG. 5 is an explanatory view showing timing of conversion to digital voltage signals in an A/D converter.

Next, operation of this X-ray image pickup apparatus for reducing deterioration of image quality due to leaks of charge signals stored in the capacitors (leakage currents) will be described using FIGS. 1-5. FIG. 5 is an explanatory view showing timing of conversion to digital voltage signals in the A/D converter. First, as shown in FIGS. 1-3, when an X-ray image pickup start is instructed at the input unit 8, the main controller 6 controls the X-ray tube controller 7 and the X-ray detection controller 12 of the X-ray detector 3. The X-ray tube controller 7 generates a tube voltage and a tube current based on the control from the main controller 6, and controls the X-ray tube 1 to emit X rays from the X-ray tube 1 to the patient M. Further, the X rays transmitted through the patient M are converted by the X-ray detecting elements 11 of the X-ray detector 3 into charge signals according to the quantity of X rays transmitted through the patient M, which are accumulated in the capacitors 20.

Then, the charge signals accumulated in the capacitors 20 will be outputted to the amplifier array 14 through the data lines DL1-DL5 when the thin-film transistors 21 acting as the switching elements are opened based on the gate actuating signal from the gate driver 13 of the X-ray detector 3. When the gate actuating signal is not outputted from the gate driver 13 of the X-ray detector 3, the thin-film transistors 21 are in the closed state. However, this closed state is imperfect, and part of the charge signals accumulated in each of the capacitors 20 of the plurality of X-ray detecting elements 11 connected to the data lines will leak and reach the amplifier array 14. As noted hereinbefore, FIG. 2 shows the X-ray detecting elements 11 arranged in the two-dimensional matrix form of five rows×five columns as an example. In the two-dimensional matrix form in the order of 4096 rows×4096 columns, the number of X-ray detecting elements 11 connected to one data line is as large as 4096, resulting in a large quantity of charge signals leaking from the capacitors 20. Also in the case of high-intensity X rays being incident on the X-ray detecting elements 11, the charge signals accumulated in the capacitors 20 become large, resulting in large charge signals leaking from the capacitors 20.

Next, based on the control from the main controller 6 (see FIG. 1), the X-ray detection controller 12 of the X-ray detector 3 first carries out control for the charge detecting amplifiers 31 in the amplifier array 14 to output the amplifier actuating signal shown in FIG. 5, and thereafter the X-ray detection controller 12 carries out control for causing the gate driver 13 to output the gate actuating signal shown in FIG. 5. FIG. 5 will now be described. In FIG. 5, each of the amplifier actuating signal, gate actuating signal, and the A/D converter is shown to be operative in the state of H level. The portion on the left-hand side of FIG. 5 shows timing for the X-ray detecting elements 11 connected to the (i−1)th data line (e.g. DL1 shown in FIG. 2), and the portion on the right-hand side of FIG. 5 timing for the X-ray detecting elements 11 connected to the i-th data line (e.g. DL2 shown in FIG. 2).

X(i) denotes an offset signal (first offset signal) which is a digital voltage signal converted by the A/D converter 4 immediately before the X-ray detection controller 12 outputs the gate actuating signal to the X-ray detecting elements 11 connected to the i-th data line (DL2). Y(i) denotes a main signal which is a digital voltage signal converted by the A/D converter 4 immediately after the X-ray detection controller 12 outputs the gate actuating signal to the X-ray detecting elements 11, and a gate operation has finished, which X-ray detecting elements 11 are connected to one predetermined gate line (i-th data line) among the plurality of gate lines. X(i−1) denotes an offset signal (second offset signal) which is a digital voltage signal converted by the A/D converter 4 immediately before output of the gate actuating signal is started after the amplifier actuating signal is outputted to the X-ray detecting elements 11 connected to the (i−1)th data line (DL1) which is one predetermined gate line adjacent the gate line (DL2) used in the operation in the first arithmetic unit 50, among the plurality of gate lines. Y(i−1) denotes a main signal which is a digital voltage signal converted by the A/D converter 4 immediately after the X-ray detection controller 12 outputs the gate actuating signal to the X-ray detecting elements 11, and a gate operation has finished, which X-ray detecting elements 11 are connected to the (i−1)th data line.

$T_L$ denotes a cycle period of the amplifier actuating signal which is a time for processing the charge signals detected by the X-ray detecting elements 11 connected to one data line. $T_{LK}$ denotes a period between an offset signal and a main signal before and after the gate actuating signal, which, for example, is a period from X(i) to Y(i), and a period from X(i−1) to Y(i−1). $T_{LK}$ is a period about 10 μs-100 μs.

Here, an operation for reducing deterioration of image quality due to charge signals leaking, for example, from the capacitors 20 of the X-ray detecting elements 11 connected to the i-th data line (DL2) shown in FIG. 2 will be described. First, the gate driver 13 outputs the gate actuating signal successively to each of the gate lines GL1-GL5. Before and after the gate actuating signal is outputted through the gate line GL1, the A/D converter 4 acquires the digital voltage signals X(i−1) and Y(i−1) shown in FIG. 5. Before and after the gate actuating signal is outputted through the gate line GL2, the A/D converter 4 acquires the digital voltage signals X(i) and Y(i) shown in FIG. 5.

Next, the first arithmetic unit 50 carries out an operation to subtract the first offset signal X(i) from the main signal Y(i), thereby to obtain a value having removed the first offset signal X(i) which is a noise component included in the main signal Y(i). This value is called a first arithmetic value Z(i). Further, the first arithmetic unit 50 outputs a signal indicating the first arithmetic value Z(i) to the correcting unit 52.

Next, the second arithmetic unit 51 carries out an operation to subtract the second offset signal X (i−1) from the first offset signal X(i), to obtain a difference between the second offset signal and the first offset signal. This can determine a quantity of charge signals having leaked from the capacitors 20 of the X-ray detecting elements 11 connected to the data line DL1 during the period from the second offset signal X (i−1) to the first offset signal X(i). This value is called a second arithmetic value L(i). The second arithmetic unit 51 outputs a signal indicating the second arithmetic value L1(i) to the correcting unit 52.

Next, the correcting unit 52 first determines a second arithmetic value L2(i) corresponding to a period of the same length as the period from the first offset signal to the main signal used in the operation in the first arithmetic unit 50. For example, as shown in FIG. 5, where $T_L/T_{LK}$ which is the ratio of the period ($T_{LK}$) from the first offset signal to the main signal used in the operation in the first arithmetic unit 50 to the period ($T_L$) from the second offset signal to the first offset signal used in the operation in the second arithmetic unit 51 is 2, $T_L/T_{LK}$=2 is stored beforehand in the period ratio memory 53 of the correcting unit 52. The correcting unit 52 reads this value, and calculates the second arithmetic value L2(i) as second arithmetic value L1(i)/($T_L/T_{LK}$). Thus, it is possible to determine charge signals leaking from the capacitors 20 of the X-ray detecting elements 11 connected to the data line DL1 during the period from the first offset signal X(i) to the main signal Y(i).

Further, the correcting unit 52 subtracts the second arithmetic value L2(i) from the first arithmetic value Z(i) calculated by the first arithmetic unit 50. This can remove the charge signals leaking from the capacitors 20 of the X-ray detecting elements 11 connected to the data line DL1 during the period from the first offset signal X(i) to the main signal Y(i).

According to the X-ray image pickup apparatus, as described above, the correcting unit 52 corrects the first arithmetic value calculated by the first arithmetic unit 50, by using the second arithmetic value calculated by the second arithmetic unit 51 and corresponding to a period of the same length as the period from the first offset signal to the main signal used in the operation in the first arithmetic unit 50. That is, the first arithmetic value is corrected to remove noise components due to leakage of the charge signals accumulated during the period from the first offset signal to the main signal. Thus, it is possible to reduce deterioration of image quality due to leaks of charge signals stored in the X-ray detecting elements 11 (leakage currents), and prevent an extended imaging time.

The multiplexer 36 receives each of the voltage signals converted by the plurality of charge detecting amplifiers 31, temporally switches the inputted voltage signals in a predetermined order, and outputs a time sharing signal bundling the voltage signals converted by each of the different charge detecting amplifiers 31. Further, the A/D converter 4 samples, with predetermined timing, each voltage signal of the time sharing signal outputted from the multiplexer 36, and converts it into each voltage signal of a digital time sharing signal. Therefore, with only one A/D converter 4 provided for the plurality of charge detecting amplifiers 31, conversion can be made from the analog voltage signals to the digital voltage signals, which realizes a reduction in the cost of conversion to the digital voltage signals.

The switching elements of the X-ray detecting elements 11 are thin-film transistors 21. Therefore, compared with switching elements such as MOSFETs, there is little deterioration of the switching elements per se due to irradiation of light or radiation. That is, use can be made for a long time. By providing a plurality of detecting devices, a detection area can be enlarged.

This invention is not limited to the foregoing embodiment, but may be modified as follows:

(1) The (i−1)th data line (DL1) has been described as one predetermined gate line used in the second arithmetic unit 51 in the foregoing embodiment for obtaining for obtaining the second offset signal, which is adjacent the (i)th gate line (DL2) used in the operation in the first arithmetic unit 50. However, this may be an adjacent data line other than the (i−1)th data line (DL1), e.g. the (i+1)th data line (DL3).

(2) In the foregoing embodiment, the correcting unit 52 has the period ratio memory 53 for storing the ratio of the period from the second offset signal to the first offset signal used in the operation in the second arithmetic unit 51, to the period from the first offset signal to the main signal used in the operation in the first arithmetic unit 50. However, the period ratio memory 53 may be provided for the second arithmetic unit 51, and when $T_L/T_{LK}$=2 which is the value stored in the period ratio memory 53 is stored for the second arithmetic value L1(i) calculated by the second arithmetic unit 51, the operation may be carried out for a second arithmetic value L1(i)/2 by the second arithmetic unit 51, and this value may be outputted as second arithmetic value L2(i) to the correcting unit 52.

Figure 6:
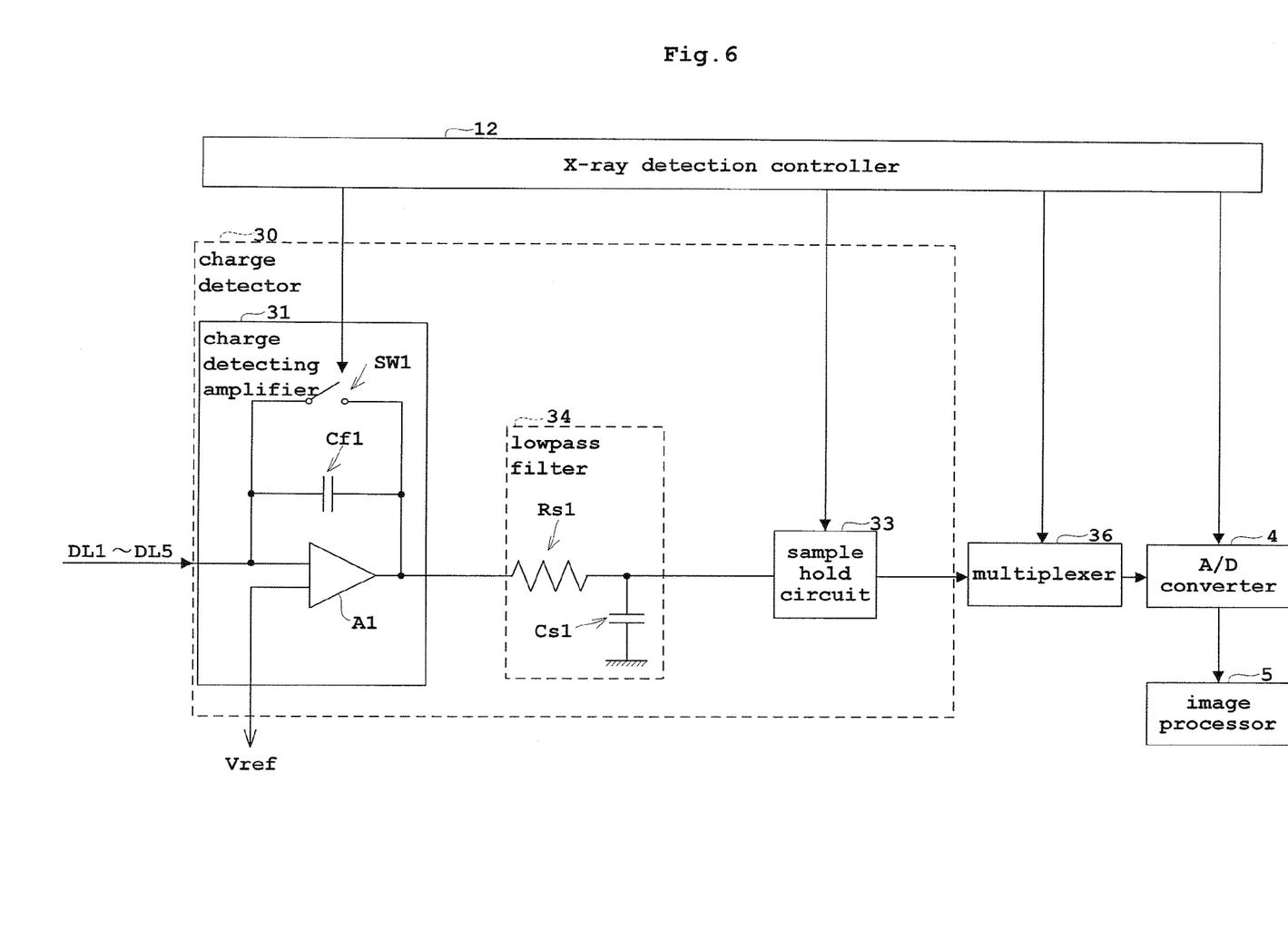
FIG. 6 is a block diagram showing an overall construction of an X-ray image pickup apparatus in modified embodiment (3).

(3) In the foregoing embodiment, the charge detector 30 has only the charge detector circuit 30. As shown in FIG. 6, it is possible to provide a charge detecting amplifier 31 for receiving charge signals outputted from each X-ray detecting element 11 and converting them into voltage signals, a lowpass filter 34 for restricting passage of signals of high frequency band components among the voltage signals converted by this charge detecting amplifier 31, and a sample hold circuit 33 for sampling the voltage signals having passed the lowpass filter 34, and holding and outputting them in a predetermined time. Thus, the lowpass filter 34 restricts passage of the signals of high frequency band components (high frequency noise) in the voltage signals converted by the charge detecting amplifier 31, and the sample hold circuit 33 samples the voltage signals having passed this lowpass filter 34, and holds them for a predetermined time. Further, stable analog voltage signals from this sample hold circuit 33 are converted into digital voltage signals. That is, the A/D converter 4 converts the stable analog voltage signals into digital voltage signals. It is also possible to reduce high frequency noise inputted to the A/D converter 4, increase the S/N ratio, and obtain high-precision images. The above sample hold circuit 33 corresponds to the holding device in this invention.

(4) The foregoing embodiment provides a plurality of charge detectors 30 (charge detecting amplifiers 31), a multiplexer 36 and one A/D converter 4. The multiplexer 36 may be omitted, and A/D converters 4 may be provided in the number corresponding to the plurality of charge detecting amplifiers 31. Thus, compared with the case of providing only one A/D converter 4 for the plurality of charge detecting amplifiers 31, the processing time in the A/D converters 4 can be shortened.

(5) In the foregoing embodiment, at least one of the main signal, first offset signal and second offset signal may be sampled two or more times to obtain an average value of these. Thus, variations in at least one signal among the main signal, first offset signal and second offset signal can be reduced to enable correction based on a high-precision value. As a result, the value corrected by the correcting unit 52 can be highly accurate.

(6) In the foregoing embodiment, filtering may be applied to at least one of the first arithmetic value in the first arithmetic unit 50, the second arithmetic value in the second arithmetic unit 51, and the first arithmetic value corrected by the correcting unit 52. That is, it is possible to obtain a weighted, optimal first arithmetic value corrected by the correcting unit 52.

(7) In the foregoing embodiment, the second arithmetic value in the second arithmetic unit 51 may be put to an averaging process using second arithmetic values in the second arithmetic unit 51 acquired in the past. For example, an averaged second arithmetic value L1'(i) may be derived from the equation:

second arithmetic value $L1'(i)=((n-1)/n) \cdot L1(i-1)+(1/n)L1(i)$ where n is a constant. Thus, an optimal second arithmetic value can be obtained. Further, the correcting unit 52 can derive an optimal first arithmetic value Z'(i) corrected by the correcting unit 52 form an equation: first arithmetic value $Z'(i)=Z(i)-L1'(i)$, using this averaged, second arithmetic value $L1'(i)$.

(8) In the foregoing embodiment, the period ($T_L$) from the second offset signal to the first offset signal used in the operation in the second arithmetic unit 51 may be the power of two of the period ($T_{LK}$) from the first offset signal to the main signal used in the operation in the first arithmetic unit 50. That is, the period ratio memory 53 stores a value corresponding to the power of two of $T_L/T_{LK}$, which simplifies a division process of the second arithmetic value $L1(i)/(T_L/T_{LK})$ for obtaining the second arithmetic value L2(i), thereby increasing the processing speed.

(9) In the foregoing embodiment, a medical apparatus has been described. The invention is applicable to fields other than medial, such as the industrial field for non-destructive testing, RI (Radio Isotope) inspection, optical inspection and so on.

(10) In the foregoing embodiment, an X-ray image pickup apparatus has been described as an example of light or radiation image pickup apparatus. Instead of being limited to X rays, the invention is applicable also to apparatus using visible light or radiation (neutron rays, gamma rays, beta rays and so on).

(11) In the foregoing embodiment, the X-ray detecting elements 11 of the X-ray detector 3 have been described as arranged in a two-dimensional matrix form of rows and columns on the X-ray detection surface S. The X-ray detecting elements 11 may be a one-dimensional line sensor of a plurality of X-ray detecting elements 11 (a plurality of X-ray detecting elements 11 connected to a data line).

(12) In the foregoing embodiment, the X-ray detecting elements 11 of the X-ray detector 3 have been described as the direct conversion type that converts X rays directly into charge signals. They may be the indirect conversion type that once converts X rays into light and converts the light into charge signals.

(13) In the foregoing embodiment, the charge detecting amplifiers 31 of the amplifier array 14 receive the charge signals outputted from the X-ray detecting elements 11, and convert them into voltage signals. The X-ray detecting elements 11 may have charge detecting amplifiers 31 to convert charge signals into voltage signals within the X-ray detecting elements 11.

The invention claimed is:

1. A light or radiation image pickup apparatus comprising (A) a plurality of detecting devices arranged in a matrix form for outputting charge signals in response to light or radiation, (B) a plurality of charge-to-voltage conversion devices the respective charge signals outputted from the plurality of detecting devices into voltage signals, (C) an A/D conversion device for receiving, sampling with predetermined timing and converting into digital voltage signals, the voltage signals converted by the plurality of charge-to-voltage conversion devices, (D) a control device for controlling the detecting devices to output the charge signals, (E) a plurality of gate lines commonly connecting the control device and the detecting devices arranged in rows, among the plurality of detecting device arranged in the matrix form, (F) a first arithmetic device for calculating a first arithmetic value by subtracting, from a main signal which is a digital voltage signal converted by the A/D conversion device immediately after the control device finishes control of the detecting devices connected to one predetermined gate line among the plurality of gate lines, a first offset signal which is a digital voltage signal converted by the A/D conversion device immediately before the control device starts the control of the detecting devices, (G) a second arithmetic device for calculating a second arithmetic value which is a difference between a second offset signal which is a digital voltage signal converted by the A/D conversion device immediately before the control device starts control of the detecting devices connected to one predetermined gate line, adjacent the gate line used in the operation in the first arithmetic device, among the plurality of gate lines, and the first offset signal used in the operation in the first arithmetic device, and (H) a correcting device for correcting the first arithmetic value calculated by the first arithmetic device, by using the second arithmetic value calculated by the second arithmetic device and corresponding to a period of the same length as a period from the first offset signal to the main signal used in the operation in the first arithmetic device.

2. The light or radiation image pickup apparatus according to claim 1, further comprising, as arranged between the charge-to-voltage conversion device and the A/D conversion device, a lowpass filter for restricting passage of signals of high frequency band components, and a holding device for sampling, and holding for a predetermined time, the voltage signals having passed the lowpass filter.

3. The light or radiation image pickup apparatus according to claim 1, further comprising a multiplexer for receiving each of the voltage signals converted by the plurality of charge-to-voltage conversion devices, temporally switching the received voltage signals in a predetermined order, and outputting a time sharing signal bundling the voltage signals converted by each of the different charge-to-voltage conversion devices, wherein the A/D conversion device samples, with predetermined timing, and converts into each voltage signal of a digital time sharing signal, each voltage signal of the time sharing signal outputted from the multiplexer.

4. The light or radiation image pickup apparatus according to claim 1, wherein the A/D conversion device corresponds in number to the plurality of charge-to-voltage conversion devices.

5. The light or radiation image pickup apparatus according to claim 1, wherein at least one of the main signal, the first offset signal and the second offset signal is sampled a plurality of times to obtain an average value thereof.

6. The light or radiation image pickup apparatus according to claim 1, wherein filtering is applied to at least one of the first arithmetic value in the first arithmetic device, the second arithmetic value in the second arithmetic device, and the first arithmetic value corrected by the correcting device.

7. The light or radiation image pickup apparatus according to claim 1, wherein the second arithmetic value in the second arithmetic device is put to an averaging process using second arithmetic values in the second arithmetic device acquired in the past.

8. The light or radiation image pickup apparatus according to claim 1, wherein the period from the second offset signal to the first offset signal used in the operation in the second arithmetic device is the power of two of the period from the first offset signal to the main signal used in the operation in the first arithmetic device.

9. The light or radiation image pickup apparatus according to claim 1, wherein the detecting devices have switching elements for outputting the charge signals based on the control of the control device, the switching elements being thin-film transistors.

* * * * *